United States Patent [19]

Haag et al.

[11] Patent Number: 4,588,714
[45] Date of Patent: May 13, 1986

[54] S-DITHIOCARBAMOYLMETHYL TRITHIOPHOSPHONATE INSECTICIDES, COMPOSITIONS AND USE

[75] Inventors: William G. Haag, Pleasant Hill; Charles G. Chavdarian, Martinez, both of Calif.

[73] Assignee: Stauffer Chemical Company, Westport, Conn.

[21] Appl. No.: 567,489

[22] Filed: Jan. 3, 1984

[51] Int. Cl.$^4$ .................. A01N 57/20; C07F 9/40
[52] U.S. Cl. .................................. 514/114; 544/157; 558/172
[58] Field of Search .................. 544/157; 546/22; 548/112, 413; 260/239 BF, 330.6, 455 P; 424/200, 212

[56] References Cited

U.S. PATENT DOCUMENTS 2,915,429  12/1959  Scherer et al. .................. 260/455 P
3,283,038  11/1966  Lorenz et al. .................. 260/455 P

FOREIGN PATENT DOCUMENTS 97576    12/1963  Denmark .
1025200   2/1958  Fed. Rep. of Germany .
1099531   2/1961  Fed. Rep. of Germany .
1116224  11/1961  Fed. Rep. of Germany .
625145    9/1961  Italy .

OTHER PUBLICATIONS

Fest et al., *The Chemistry of Phosphorus Pesticides*, 2nd Revised Ed. (1982), pp. 128 and 337.
Eto, *Organophosphorus Pesticides: Organic and Biological Chemistry*, (1974), pp. 55-56, 257, 266-268.

Primary Examiner—Robert W. Ramsuer
Attorney, Agent, or Firm—Joel G. Ackerman

[57] ABSTRACT

Compounds and compositions containing them, for insecticidal control having the formula

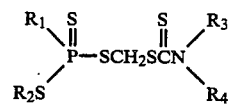

in which $R_1$ is an alkyl group having from 1 to 3 carbon atoms, $R_2$ is an alkyl group having from 1 to 6 carbon atoms, and $R_3$ and $R_4$ are independently alkyl groups having from 1 to 6 carbon atoms, or $R_3$ and $R_4$ taken together form a ring having the formula

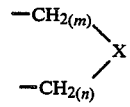

in which m and n are each integers from 1 to 3 and X is oxygen or —$CH_2$—, together with insecticidal compositions containing such compounds, and methods for controlling insects.

24 Claims, No Drawings

S-DITHIOCARBAMOYLMETHYL TRITHIOPHOSPHONATE INSECTICIDES, COMPOSITIONS AND USE

This invention relates to a series of trithiophosphonate insecticides having the formula

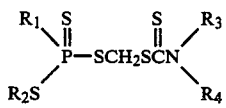

in which $R_1$ is an alkyl group having from 1 to 3 carbon atoms, $R_2$ is an alkyl group having from 1 to 6 carbon atoms, and $R_3$ and $R_4$ are independently alkyl groups having from 1 to 6 carbon atoms, or $R_3$ and $R_4$ taken together form a ring having the formula

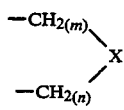

in which m and n are each integers from 1 to 3 and X is oxygen or —$CH_2$— together with insecticidal compositions containing such compounds, and methods for their use in controlling insects.

Preferably $R_2$ is an n-propyl group or a branched chain alkyl group having from 3 to 6 carbon atoms, and most preferably a branched chain alkyl in which the branching is at the alpha- or beta-carbon atom. Examples of preferred groups for $R_2$ are n-propyl, isopropyl, sec-butyl, tertiary butyl and 1,1-dimethylpropyl. $R_3$ and $R_4$ may be the same or different alkyl groups, but are preferably identical and contain 1–4 carbon atoms each. In compounds in which $R_3$ and $R_4$ are combined into a ring configuration

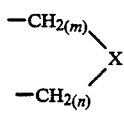

m and n are preferably 1 or 2 and X is preferably oxygen. $R_1$ is preferably methyl or ethyl.

The term "insects" as used herein refers to the broad and commonly understood usage rather than to those creatures which in the strict biological sense are classified as insects, and includes, in addition to those belonging to the class Insecta, some classes of acarids such as spiders, mites, ticks, and the like, particularly mites.

As will be seen from the data which follows, the compounds of this invention demonstrate activity in controlling varous types of insects, and particularly mites and aphids.

The compounds of the present invention may be prepared according to the reaction scheme shown below:

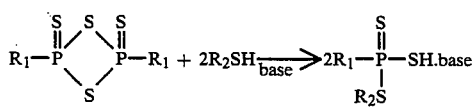

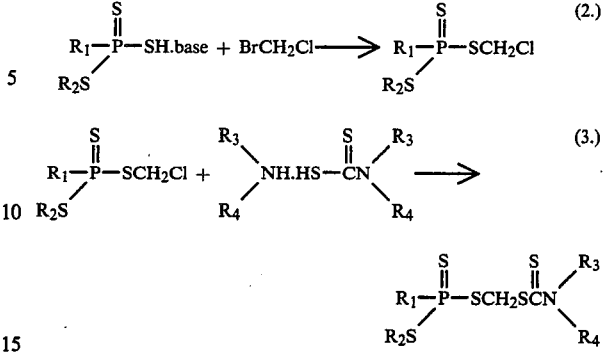

In the first step the appropriate alkyl thionophosphine sulfide is reacted with two equivalents of a desired mercaptan in the presence of a base to produce a thioic acid salt. The starting material sulfide may be obtained for instance by the procedure described in P. E. Newallis, et al., Journal of Organic Chemistry, 1962, Vol. 27, p. 3829. Reaction 1 is advantageously carried out at a temperature of from about −40° C. to about 150° C., preferably from about 0° C. to about 70° C., in an organic solvent in the presence of a base, particularly a tertiary amine. Suitable solvents include aromatic hydrocarbons such as benzene or toluene, ethers such as diethyl ether or tetrahydrofuran, and ketones such as acetone. Suitable tertiary amines include triethylamine, dimethylaniline, diethylaniline, and pyridine. Inorganic bases such as sodium hydroxide could be used in this step, but are less desirable as the resulting salts are less soluble in the solvents utilized. As the reaction is exothermic, the base is preferably added dropwise when operating on the laboratory scale. The product may be recovered by evaporating or distilling off the solvent.

In the second step the thioic acid salt is reacted with bromochloromethane to produce an S-chloromethyl dialkyltrithiophosphonate. This reaction is conducted in an organic solvent such as that utilized in the first step, at a temperature of from about 20° C. to about 130° C., preferably from about 20° to about 70° C. The bromochloromethane reagent is utilized in excess in this step. The product may be recovered by removing precipitated salts, followed by evaporating or distilling off the solvent, and purifying by distillation or chromatography.

In the third step, the S-chloromethyldialkyl trithiophosphonate is reacted with an N,N-dialkyldithiocarbamoyl-dialkylamine salt to produce the compound of the invention. This reaction is conducted in an organic solvent such as that utilized in the first step, or in an alcohol such as ethanol, at a temperature of from about 0° C. to 130° C., preferably from about 20° to about 115° C. The N,N-dialkyldithiocarbamoyl-dialkylamine salt is initially prepared by reaction of carbon disulfide with two equivalents of the appropriate secondary amine. Suitable secondary amines are saturated dialkylamines and cyclic amines such as morpholine, piperidine, and pyrrolidine. The desired product may be recovered by evaporating or distilling off the solvent, and further purifying.

The following represent examples of the preparation of compounds of this invention.

EXAMPLE I

Preparation of S-n-Propyl
S-(N,N-diethyldithiocarbamoylmethyl)
Ethylphosphonotrithioate (Compound 10 herein)

(a) To a slurry of 6.0 grams (g) (0.0242 mole) of ethylthionophosphine sulfide in 40 milliliters (ml) of tetrahydrofuran, under nitrogen and at room temperature, was added 4.6 ml (3.87 g, 0.0508 mole) of n-propyl-mercaptan. To the resultant solution was added 7.1 ml (5.14 g, 0.0508 mole) of triethylamine dropwise and the reaction mixture was refluxed for 4 hours. After cooling, the mixture was evaporated to give 13.51 g (93% of theoretical yield) of a viscous oil, the triethylamine salt of S-n-propyl ethylphosphonotrithioic acid.

(b) To a solution of 5.8 ml (11.59 g, 0.0897 mole) of bromochloromethane in 15 ml of tetrahydrofuran and under nitrogen was added a solution of 9.0 g (0.0299 mole) of the triethylamine salt [obtained in step (a)] in 25 ml of tetrahydrofuran. The mixture was refluxed for 4 hours, and then cooled and filtered. To the filtrate was added 50 ml of ether. The ethereal solution was washed with 50 ml of water and 50 ml of saturated aqueous sodium chloride, dried with magnesium sulfate, and evaporated to an oil. Bulb-to-bulb distillation [oven temperature 85°–95° C. (0.025 torr)] afforded 4.11 g (55% of theoretical yield) of S-n-propyl S-chloromethyl ethylphosphonotrithioate, a clear colorless oil. The structure of the product was confirmed by nuclear magnetic resonance, infrared and mass spectroscopy.

(c) To a solution of 0.53 ml (0.673 g, 0.0088 mole) of carbon disulfide in 5 ml of tetrahydrofuran, at 0° C. and under nitrogen, was added dropwise a solution of 1.87 ml (1.29 g, 0.0177 mole) of diethylamine in 15 ml of tetrahydrofuran. After stirring for 15 minutes at room temperature, a solution of 2.0 g (0.008 mole) of the product from step (b) in 5 ml of tetrahydrofuran was added. The reaction mixture was refluxed for 5 hours. After cooling, 10 ml of water was added and the mixture was extracted with ether (3×10 ml). The ethereal layers were combined, washed with 20 ml of water and 20 ml of saturated aqueous sodium chloride, and dried with magnesium sulfate. Evaporation of the solution yielded a yellow oil. Purification by a preparative, centrifugally accelerated, thin-layer (4 mm, silica gel) chromatograph with 98:2 hexane-acetone as eluent, afforded 1.90 g (65% of theoretical yield) of the desired compound, a clear viscous oil. The structure was confirmed by nuclear magnetic resonance, infrared and mass spectroscopy.

EXAMPLE II

Preparation of S-sec-Butyl
S-(N,N-di-n-propyldithiocarbamoylmethyl)
Ethylphosphonotrithioate (Compound 11 herein)

(a) Following the procedure as shown in Example 1, step (a), 14.67 g (94%) of the triethylamine salt of S-sec-butyl ethylphosphonotrithioic acid was obtained from 6.0 g (0.0242 mole) of ethylthionophosphine sulfide, 5.80 ml (4.58 g, 0.0508 mole) of sec-butyl mercaptan, and 7.1 ml (5.14 g, 0.0508 mole) of triethylamine.

(b) Following the procedure as shown in Example I, step (b), 9.0 g (0.0285 mole) of the triethylamine salt from step (a) and 5.6 ml (11.10 g, 0.0855 mole) of bromochloromethane afforded 4.10 g (55%) of distilled S-sec-butyl S-chloromethyl ethylphosphonotrithioate [oven temperature 94°–100° C. (0.03 torr)].

(c) Following the procedure as shown in Example I, step (c), 0.87 g (30%) of the title compound was obtained from 0.49 ml (0.62 g, 0.0082 mole) of carbon disulfide, 2.3 ml (1.69 g, 0.0164 mole) of di-n-propylamine, and 2.0 g (0.0074 mole) of the product from step (b). The structure was confirmed by nuclear magnetic resonance, infrared and mass spectroscopy.

EXAMPLE III

Preparation of S-t-Butyl
S-(morpholinothiocarbonylthiomethyl)
Ethylphosphonotrithioate (Compound 4 herein)

To a solution of 0.274 ml (0.347 g, 0.0046 mole) of carbon disulfide in 20 ml of ethanol was added 0.80 ml (0.80 g, 0.0091 mole) of morpholine. A white mixture resulted. The mixture was heated to reflux and a solution of 1.0 g (0.0038 mole) of S-t-butyl S-chloromethyl ethylphosphonotrithioate in 3 ml at ethanol was added. (The S-t-butyl S-chloromethyl ethylphosphonotrithioate was prepared according to the procedure of Example I, steps (a) and (b), from ethylthionophosphine sulfide, t-butyl mercaptan, triethylamine, and bromochloromethane.) The mixture was refluxed for 16 hours. After cooling, 20 ml of water was added and the mixture was twice extracted with ether. The ethereal solution was washed with 20 ml of water and 20 ml of brine, dried with magnesium sulfate, and evaporated to a viscous oil. Purification by a preparative, centrifugally accelerated, thin-layer (4 mm, silica gel) chromatograph, with 9:1 hexane-acetone as eluent, afforded 0.39 g (28% of theoretical yield) of the title compound, a clear, viscous oil. The structure was confirmed by nuclear magnetic resonance, infrared and mass spectroscopy.

The following Table I depicts representative compounds of this invention, which may be prepared by the process previously described. Structures of these compounds were confirmed by analysis as above. All compounds of Table I were obtained in the form of highly viscous oils.

TABLE I $$\begin{array}{c} R_1 \diagdown \overset{S}{\underset{\|}{}} \quad\quad \overset{S}{\underset{\|}{}} \diagup R_3 \\ P-SCH_2SCN \\ R_2S \diagup \quad\quad\quad \diagdown R_4 \end{array}$$

| Compound Number | $R_1$ | $R_2$ | $R_3$ | $R_4$ |
|---|---|---|---|---|
| 1 | $C_2H_5$ | $C(CH_3)_3$ | $C_2H_5$ | $C_2H_5$ |
| 2 | $C_2H_5$ | $C(CH_3)_3$ | $n\text{-}C_3H_7$ | $n\text{-}C_3H_7$ |
| 3 | $C_2H_5$ | $C(CH_3)_3$ | $i\text{-}C_4H_9$ | $i\text{-}C_4H_9$ |
| 4 | $C_2H_5$ | $C(CH_3)_3$ | \multicolumn{2}{c}{morpholino} |
| 5 | $C_2H_5$ | $C(CH_3)_3$ | $CH_3$ | $CH_3$ |
| 6 | $CH_3$ | $C(CH_3)_2C_2H_5$ | $C_2H_5$ | $C_2H_5$ |
| 7 | $C_2H_5$ | $sec\text{-}C_4H_9$ | $C_2H_5$ | $C_2H_5$ |
| 8 | $C_2H_5$ | $n\text{-}C_3H_7$ | $n\text{-}C_3H_7$ | $n\text{-}C_3H_7$ |
| 9 | $C_2H_5$ | $i\text{-}C_3H_7$ | $n\text{-}C_3H_7$ | $n\text{-}C_3H_7$ |
| 10 | $C_2H_5$ | $n\text{-}C_3H_7$ | $C_2H_5$ | $C_2H_5$ |
| 11 | $C_2H_5$ | $sec\text{-}C_4H_9$ | $n\text{-}C_3H_7$ | $n\text{-}C_3H_7$ |
| 12 | $C_2H_5$ | $i\text{-}C_3H_7$ | $C_2H_5$ | $C_2H_5$ |
| 13 | $CH_3$ | $C(CH_3)_3$ | $n\text{-}C_3H_7$ | $n\text{-}C_3H_7$ |
| 14 | $CH_3$ | $C(CH_3)_3$ | $C_2H_5$ | $C_2H_5$ |
| 15 | $CH_3$ | $i\text{-}C_3H_7$ | $n\text{-}C_3H_7$ | $n\text{-}C_3H_7$ |
| 16 | $CH_3$ | $i\text{-}C_3H_7$ | $C_2H_5$ | $C_2H_5$ |
| 17 | $C_2H_5$ | $C_2H_5$ | $C_2H_5$ | $C_2H_5$ |

TABLE I-continued

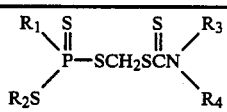

| Compound Number | $R_1$ | $R_2$ | $R_3$ | $R_4$ |
|---|---|---|---|---|
| 18 | $C_2H_5$ | $C_2H_5$ | $n\text{-}C_3H_7$ | $n\text{-}C_3H_7$ |

Insecticidal Evaluation Tests

The compounds in Table I above were tested for insecticidal activity using the following testing procedures. LD-50 values, based on the results of these tests, and calculated according to dosage-mortality curves, are expressed in Table II.

Housefly [*Musca domestica*]

Test compounds were diluted in acetone and aliquots pipetted onto the bottom of aluminum dishes. To insure even spreading of the chemical on the bottom of the dishes, 1 ml of acetone containing 0.01% peanut oil was also added to each dish. After all solvents had evaporated, the dishes were placed in circular cardboard cages containing 25 female houseflies, 1-2 days old. The cages were covered on the bottom with cellophane and on the top with tulle netting, and each contained a sugar-water saturated cotton plug for maintenance of the flies. Mortality was recorded after 48 hours. Test levels ranged from 100 μg/25 female houseflies downward. The LD-50 values are expressed below in Table II under the heading "HF-C", in terms of μg of the test compound per 25 female flies.

Black Bean Aphid [*Aphis fabae* (Scop.)]

Nasturtium plants (Tropaeolum sp.) approximately 5 cm tall, were transplanted into sandy loam soil in 3-inch clay pots and infested with 25-50 black bean aphids of mixed ages. Twenty-four hours later they were sprayed to the point of runoff with 50-50 acetone-water solutions of the test compounds. Treated plants were held in the greenhouse and mortality was recorded after 48 hours. Test concentrations ranged from 0.05% downward. The LD-50 values are expressed below in Table II under the heading "BA-C" in terms of percent of the test compound in the sprayed solution.

Tobacco Budworm [*Heliothis virescens* (Fabricius)]

(a) Contact: Test compounds were diluted in a 50-50 acetone-water solution. Cotton (Gossypium sp.) cotyledons were immersed in the test solutions for 2-3 seconds and placed on a wire screen to dry. The dried leaves were placed in petri dishes containing a moistened piece of filter paper and infested with 5 second-instar tobacco budworm larvae. The dishes were placed in a high humidity chamber for 5 days, and percent mortality of the larvae recorded. Test concentrations ranged from 0.1% downward. The LD-50 values are expressed below in Table II under the heading "TBW-C" in terms of the test compound in the solution.

(b). Eggs: Paper towel patches of 2-day old eggs of the tobacco budworm were dipped in acetone solutions of the test compounds and placed in petri dishes containing a portion of larval rearing medium. Treated eggs were maintained at 78° F. and mortality was recorded after all control eggs had hatched and the young larvae were feeding on the media. Test concentrations ranged from 0.1% downward. The LD-50 values are expressed below in Table II under the heading "TBW-E" in terms of percent of the test compound in the solution.

Beet Armyworm (*Spodoptera exigua*)

Test compounds were diluted in a 50—50 acetone-water solution. Young leaves of sugar beets (*Beta vulgaris*) were immersed in the test solutions for 2-3 seconds and placed on a wire screen to dry. The dried leaves were placed in petri dishes containing a moistened filter paper and infested with five second-instar beet armyworm larvae. The dishes were placed in a high humidity chamber. Mortality of the larvae was recorded five days later. Test concentrations ranged from 0.1% downward. The LD-50 values are expressed below in Table II under the heading "BAW" in terms of percent of the test compound in solution.

Cabbage Looper [*Trichoplusia ni* (Hubner)]

Test compounds were diluted in a 50—50 acetone-water solution. Cotyledons of hyzini squash (*Calabacita abobrinha*), approximately 1×0.5 inches, were immersed in the test solutions for 2-3 seconds and placed on a wire screen to dry. The dried leaves were placed in petri dishes containing a moistened piece of filter paper and infested with 5 second-instar cabbage looper larvae. The dishes were placed in a high humidity chamber. Mortality of the larvae was recorded 5 days later. Test concentrations ranged from 0.1% downward. The LD-50 values are expressed below in Table II under the heading "CL" in terms of percent of the test compound in this solution.

German Cockroach [*Blatella germanica* (Linn.)]

Test compounds were diluted in a 50—50 acetone-water solution. Two ml of the solution was sprayed through a hand spray gun into circular cardboard cages containing 10 one-month old German cockroach nymphs. The test cages were covered on the bottom with cellophane and on the top with tulle netting. Percent mortality was recorded 4 days later. Test concentrations ranged from 0.1% downward. The LD-50 values are expressed below in Table II under the heading "GR" in terms of percent of the test compound in the sprayed solution.

Lygus Bug [*Lygus hesperus* (Knight)]

Test compounds were diluted in a 50—50 acetone-water solution. Two ml of the solution was sprayed through a hand-spray gun into circular cardboard cages containing 1 green bean pod and 10 adult lygus bugs. The test cages were covered on the bottom with cellophane and on the top with tulle netting. Percent mortality was recorded 48 hours later. Test concentrations ranged from 0.05% downward. The LD-50 values are expressed below in Table II under the heading "LB" in terms of percent of the test compound in the sprayed solution.

Western Spotted Cucumber Beetle Larve [*Diabrotica undecimpunctata* (Mannherheim)]

Ten grams of moist potting soil was placed in a plastic cup. Test compounds were dissolved in acetone or another appropriate solvent. A 0.05 ml aliquot of the test sample, diluted to the desired concentration, was added to the soil. The cup was capped and the soil was mixed on a vortex mixer for aproximately 15 seconds. An indentation was made on the surface of the soil and approximately 50 Diabtrotica eggs were added. The eggs were covered with soil and maintained at room temperature (approximately 70° F. or 21° C.). Four days later a section of Romaine lettuce (*Latuca sativa*) leaf was placed in the treated cups. One week later the cups were examined for live larvae. Test concentrations ranged from 25 ppm downward. The LD-50 values are expressed below in Table II under the heading "Diabrotica" in terms of ppm of the test compound in the solution.

Acaricidal Evaluation Test

The two-spotted mite (2SM) [*Tetranychus urticae* (Koch)] was employed in tests for miticides. The test procedure was as follows:

Pinto bean plants (Phaseolus sp.) approximately 10 cm tall, were transplanted into sandy loam soil in 3-inch clay pots and thoroughly infested with two-spotted mites of mixed ages and sexes. Twenty-four hours later the infested plants were inverted and dipped for 2-3 seconds in 50—50 acetone-water solutions of the test compounds. Treated plants were held in the greenhouse, and 7 days later mortality was determined for both adult mites and the nymphs hatching from eggs which were on the plants at the time of treatment. Test concentrations ranged from 0.05% downward. The LD-50 values are expressed below in Table II under the headings "2SM-A" (i.e., adults) and "2SM-E" (i.e., eggs) in terms of percent concentration of the test compound in the solution.

compound or compounds, various carriers or diluents; surface-active agents (wetting agents, dispersing agents and/or emulsifying agents); solvents (water, or organic solvents such as aromatic solvents or chlorinated aliphatic solvents); adhesives; thickeners; binders; antifoaming agents; and other substances as mentioned herein. Solid carriers or diluents included in such compositions or formulations may include, for example, ground natural minerals such as kaolins, alumina, calcium carbonate, silica, kieselguhr, clays, etc.; ground synthetic minerals such as various silicates and aluminosilicates and ground vegetable products such as bark, cornmeal, sawdust, cellulose powder and the like.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles.

Wettable powders and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of akali and alkaline earth metal salts of fatty acids.

Emulsifiable concentrates are generally obtained by dissolving the active compound in an organic solvent,

TABLE II

| Cmpd. No. | HF, μg | BA, % | 2-SM A, % | 2-SM E, % | TBW (LD$_{50}$) C, % | TBW (LD$_{50}$) E, % | BAW, % | CL, % | GR, % | LB, % | Diabrotica, ppm |
|---|---|---|---|---|---|---|---|---|---|---|---|
| 1 | 39 | 0.03 | <0.0003 | 0.0006 | 0.003 | >0.1 | 0.03 | 0.006 | 0.05 | 0.03 | 7.5 |
| 2 | 31 | 0.05 | 0.001 | 0.006 | 0.001 | 0.03 | 0.05 | 0.006 | 0.03 | 0.04 | 3 |
| 3 | >100 | >0.05 | 0.003 | 0.003 | 0.005 | 0.08 | — | — | — | — | 7.5 |
| 4 | 28 | 0.001 | 0.0006 | 0.006 | 0.03 | — | 0.03 | 0.03 | 0.08 | 0.03 | >10 |
| 5 | 38 | 0.002 | 0.002 | 0.003 | 0.01 | 0.03 | 0.03 | 0.01 | 0.04 | 0.006 | >25 |
| 6 | >100 | 0.002 | 0.001 | 0.006 | 0.03 | 0.008 | 0.03 | 0.03 | — | — | 7.5 |
| 7 | 7 | 0.002 | 0.0003 | 0.003 | 0.006 | 0.1 | 0.01 | 0.03 | — | — | 7.5 |
| 8 | <100 | 0.03 | 0.002 | 0.006 | 0.08 | 0.1 | >0.1 | 0.03 | >0.1 | >0.05 | 7.5 |
| 9 | <100 | 0.01 | 0.002 | 0.003 | 0.03 | 0.1 | 0.08 | 0.03 | >0.1 | >0.05 | 2 |
| 10 | <100 | 0.0001 | 0.0003 | 0.0006 | 0.05 | 0.1 | 0.08 | 0.03 | >0.1 | >0.05 | 17 |
| 11 | <100 | 0.01 | 0.0002 | 0.0006 | 0.05 | 0.02 | 0.08 | 0.007 | >0.1 | >0.05 | 7.5 |
| 12 | <100 | 0.003 | 0.002 | 0.006 | 0.03 | 0.1 | 0.05 | 0.03 | >0.1 | >0.05 | 3 |
| 13 | >100 | >0.05 | 0.002 | 0.002 | 0.003 | 0.03 | 0.03 | <0.003 | — | — | 3 |
| 14 | <100 | 0.05 | 0.001 | 0.006 | 0.025 | 0.1 | 0.03 | 0.025 | — | — | >25 |
| 15 | <100 | 0.03 | 0.006 | 0.006 | >0.1 | >0.1 | — | — | —. | — | >25 |
| 16 | <100 | 0.01 | 0.003 | 0.006 | 0.08 | >0.1 | 0.04 | 0.03 | — | — | 7.5 |
| 17 | <100 | 0.05 | 0.006 | 0.003 | 0.08 | >0.1 | >0.1 | 0.1 | — | — | >25 |
| 18 | >100 | >0.05 | 0.05 | 0.05 | >0.1 | 0.1 | — | — | — | — | 2 |

Key:
C = Contact Test
E = Test on eggs
A = Test on adults

In practice, a pure compound can be used as an insecticide. However, in general, the compounds are first formulated with one or more inert (i.e. non-chemically reactive, plant compatible or herbicidally inert) carriers or diluents suitable for insecticidal use, before being applied.

The compositions or formulations, including a compound as described herein, may take any one of a number of solid or liquid forms. Examples of solid forms are dusts, granules, tablets, powders and the like. Examples of liquid forms are emulsions, solutions, suspensions, flowables, emulsifiable concentrates and pastes. Such compositions may contain, in addition to the active for example, butanol, cyclohexanone, xylenes, or higher boiling aromatic hydrocarbons. To obtain suspensions or emulsions in water, wetting agents may also be added.

Flowables are prepared by mixing an active compound with one or more dispersing agents and/or solid additives, and a liquid (which may be water or an organic solvent in which the active compound is relatively insoluble, and grinding the mixture.

Both liquid and solid compositions may be in microcapsule or encapsulated form, to permit release of the enclosed active compound at a controlled rate over a period of time. Liquid compositions of this type contain encapsulated droplets of approximately 1–50 microns in diameter, including the active compound and optionally a solvent. The encapsulating material is an inert porous membrane of a polymeric material.

Solid encapsulated compositions generally take the form of granules, in which the liquid containing the active component is trapped in the pores of the granular support by a porous polymeric membrane through which the active ingredient may migrate at a controlled rate, or which membrane breaks down at a controlled rate to permit escape of the active ingredient.

Typical encapsulating materials include natural and synthetic rubbers, cellulosic materials, styrene-butadiene copolymers, polyacrylonitriles, polyacrylates, polyamides, polyisocyanates, polyurethanes, mixed copolymers of the foregoing and starch xanthates.

It is possible to use highly concentrated liquid compositions containing up to about 95% by weight of the active compound, or even the 100% active compound alone, when applying the compound in the form of a finely divided liquid by use of various atomizing equipment, for example by airplane spraying techniques. For other purposes, however, the various types of compositions which can be utilized for these compounds will contain varying amounts of the compound according to the type of composition and the intended use.

In general, insecticidal compositions may contain from 5 to 95% of the active compound, more preferably from 10 to 85%. Some typical compositions will contain an active compound as follows: wettable powders: 25 to 80% active compound; oil suspensions, emulsions, solutions, flowables, and emulsifiable concentrates: 5 to 85% active compound; aqueous suspensions: 20 to 50% active compound; dusts and powders: 5 to 20% active compound; granules and pellets: 5 to 20% active compound.

In addition to the active compound and the various agents utilized in preparing compositions and formulations mentioned, such compositions may also contain one or more other active compounds of the type mentioned herein as well as other active pesticidal agents, such as herbicides, fungicides, insecticides, acaricides, nematocides, bactericides, and plant growth regulators. Such compounds may also contain soil disinfectants or fumigants and may further contain fertilizers, thus making it possible to provide multi-purpose compositions containing one or more of the active compounds described herein as well as, optionally, other pesticides and also fertilizers, all intended and formulated for use at the same locus.

Control of insect pests is accomplished by applying a composition containing an insecticidally effective amount of an active compound as described herein to the insect, to a locus at which insecticidal control is desired, or to food sources (including seeds) on which the insects feed. For use in the last mentioned manner it is preferable to utilize a compound which is not volatile. Thus, control may be achieved by direct application of the active compounds to the insects and indirectly by application of the compounds to a locus to be protected (such as crop lands, grass ranges and forests), to a source of food for insects or to other insect habitats (for example, breeding or swarming areas). The rates of application of the active compound, and the concentration applied, will vary according to whether the compound or composition is being directly applied to the insect or indirectly, to a locus, food or habitat. In the latter case the rate of the application, depending on the nature of the insect or insects to be controlled, and the plant environment, will generally vary from about 0.01 to about 100 pounds per acre (about 0.112 to about 112 kg/ha).

It should be noted that the active compound need not be insecticidally active per se to effect insect control. The purposes of this invention are fully served if such compounds are rendered active by external influences, such as light or heat, or by some physiological action which occurs when the compound is ingested into the body of the insect.

Compositions containing one or more of the active compounds described, in an insecticidally effective amount, may be applied to the plant, locus or insect habitat in any conventional manner.

When used in connection with crop or other plant protection, application may be made in a preventive (i.e. before infestation) or eradicative manner (i.e., after infestation). Thus, powders and various liquid compositions containing the active compound can be applied by the use of power dusters, boom and hand sprayers and spray dusters, or applied from airplanes as dusts or sprays. When applied in the latter method they may be effective in very low dosages.

Compositions including active compounds may also be applied by addition to irrigation waters supplied to the field to be treated. This method of application permits penetration of the compounds into the soil as the water is absorbed therein.

Compositions including active compounds may additionally be used to protect plant seeds from being attacked by soil-borne insect pests after planting and during germination, by applying the composition to the seeds as a seed dressing. This is performed generally by mixing the seeds with an active composition in either liquid or solid form (preferably liquid) in a suitable mixing apparatus. Liquid compositions for this purpose may contain an adhesive or sticking agent, such as methyl cellulose, ethyl cellulose, etc., to assist the composition in adhering to the seed. If a solid composition is utilized for this purpose, an adhesive agent may be sprayed on the seeds during or after mixing.

For use as a soil insecticide, the active compound, or compositions containing it, may be mixed with the soil in any conventional manner, before, during or after planting of the plant seeds. Liquid compositions may be applied by spraying onto the surface or by incorporation in irrigation or sprayed water. Solid or liquid compositions containing an active compound may be incorporated into the soil prior to or during planting by discing, plowing or other mixing operations, in order to locate the active ingredient below the surface of the soil so as to be most effective in controlling undesirable larvae.

Some examples of compositions containing the active compounds of this invention are:

| Component | | Weight % |
|---|---|---|
| Composition A: Granular Solid | | |
| Compound 1 | | 10 |
| attapulgite clay granules | | 90 |
| | Total | 100% |
| Composition B: Wettable Powder | | |
| Compound 4 | | 80 |
| wetting agent (sodium dialkyl- | | 1 |

| Component | Weight % |
|---|---|
| naphthalene sulfonate) | |
| dispersing agent (sodium lignosulfonate) | 4 |
| diluent (aluminum magnesium silicate) | 15 |
| Total | 100% |
| Composition C: Dilute Solution | |
| Compound 7 | 5 |
| solvent (xylene) | 95 |
| Total | 100% |
| Composition D: Emulsifiable Concentrate | |
| Compound 10 | 50 |
| Emulsifier (blend of metal sulfonates and polyoxyethylene ethers) | 10 |
| solvent (xylene) | 40 |
| Total | 100% |
| Composition E: Concentrated Solution | |
| Compound 11 | 90 |
| solvent (xylene) | 10 |
| Total | 100% |

What is claimed is:

1. A compound having the formula

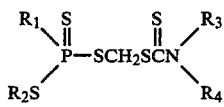

in which $R_1$ is an alkyl group having from 1 to 3 carbon atoms, $R_2$ is an alkyl group having from 3 to 6 carbon atoms, and $R_3$ and $R_4$ are independently alkyl groups having from 2 to 4 carbon atoms.

2. A compound according to claim 1 in which $R_2$ is a branched chain alkyl group having from 3 to 6 carbon atoms.

3. A compound according to claim 1 in which $R_3$ and $R_4$ are identical alkyl groups.

4. A compound according to claim 1 wherein $R_1$ is ethyl, $R_2$ is tertiary butyl, $R_3$ is ethyl and $R_4$ is ethyl.

5. A compound according to claim 1 wherein $R_1$ is ethyl, $R_2$ is tertiary butyl, $R_3$ is n-propyl and $R_4$ is n-propyl.

6. A compound according to claim 1 wherein $R_1$ is ethyl, $R_2$ is tertiary butyl, $R_3$ is isobutyl and $R_4$ is isobutyl.

7. A compound according to claim 1 wherein $R_1$ is methyl, $R_2$ is 1,1-dimethylpropyl, $R_3$ is ethyl and $R_4$ is ethyl.

8. A compound according to claim 1 wherein $R_1$ is ethyl, $R_2$ is sec-butyl, $R_3$ is ethyl and $R_4$ is ethyl.

9. A compound according to claim 1 wherein $R_1$ is ethyl, $R_2$ is n-propyl, $R_3$ is n-propyl and $R_4$ is n-propyl.

10. A compound according to claim 1 wherein $R_1$ is ethyl, $R_2$ is isopropyl, $R_3$ is n-propyl and $R_4$ is n-propyl.

11. A compound according to claim 1 wherein $R_1$ is ethyl, $R_2$ is n-propyl, $R_3$ is ethyl and $R_4$ is ethyl.

12. A compound according to claim 1 wherein $R_1$ is ethyl, $R_2$ is sec-butyl, $R_3$ is n-propyl and $R_4$ is n-propyl.

13. A compound according to claim 1 wherein $R_1$ is ethyl, $R_2$ is isopropyl, $R_3$ is ethyl and $R_4$ is ethyl.

14. A compound according to claim 1 wherein $R_1$ is methyl, $R_2$ is tertiary butyl, $R_3$ is n-propyl and $R_4$ is n-propyl.

15. A compound according to claim 1 wherein $R_1$ is methyl, $R_2$ is tertiary butyl, $R_3$ is ethyl and $R_4$ is ethyl.

16. A compound according to claim 1 wherein $R_1$ is methyl, $R_2$ is isopropyl, $R_3$ is n-propyl and $R_4$ is n-propyl.

17. A compound according to claim 1 wherein $R_1$ is methyl, $R_2$ is isopropyl, $R_3$ is ethyl and $R_4$ is ethyl.

18. A method for controlling insects comprising applying to said insect or a locus at which control is desired an insecticidally effective amount of a compound having the formula

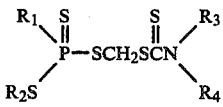

in which $R_1$ is an alkyl group having from 1 to 3 carbon atoms, $R_2$ is an alkyl group having from 3 to 6 carbon atoms, and $R_3$ and $R_4$ are independently alkyl groups having from 2 to 4 carbon atoms.

19. A method according to claim 18 in which $R_2$ is a branched chain alkyl group having from 3 to 6 carbon atoms.

20. A method according to claim 18 in which $R_3$ and $R_4$ are identical alkyl groups.

21. A method according to claim 18 in which the insect to be controlled is an acarid.

22. A method according to claim 18 in which the insect to be controlled is a mite.

23. A method according to claim 18 in which the insect to be controlled is an aphid.

24. An insecticidal composition comprising
(a) an insecticidally effective amount of a compound of the formula

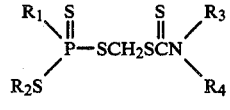

in which $R_1$ is an alkyl group having from 1 to 3 carbon atoms, $R_2$ is an alkyl group having from 3 to 6 carbon atoms, and $R_3$ and $R_4$ are independently alkyl groups having from 2 to 4 carbon atoms and
(b) an inert carrier or diluent.

* * * * *